United States Patent [19]

Ohashi et al.

[11] 4,297,282
[45] Oct. 27, 1981

[54] RESOLUTION OF MERCAPTOPROPIONIC ACIDS

[75] Inventors: Naohito Ohashi, Nishinomiya; Shoji Nagata; Junki Katsube, both of Toyonaka, all of Japan

[73] Assignee: Sumitomo Chemical Company, Limited, Osaka, Japan

[21] Appl. No.: 90,857

[22] Filed: Nov. 2, 1979

[30] Foreign Application Priority Data

| Mar. 2, 1979 | [JP] | Japan | 54-24820 |
| Mar. 2, 1979 | [JP] | Japan | 54-24821 |
| Mar. 13, 1979 | [JP] | Japan | 54-29548 |
| Jun. 28, 1979 | [JP] | Japan | 54-82412 |
| Jul. 25, 1979 | [JP] | Japan | 54-95228 |

[51] Int. Cl.³ .............. C07D 207/16; C07C 153/017
[52] U.S. Cl. .............................. 260/326.2; 260/455 R
[58] Field of Search ..................... 260/326.2, 455 R

[56] References Cited

U.S. PATENT DOCUMENTS

| 3,739,019 | 6/1973 | Ueda et al. | 562/401 |
| 3,954,870 | 5/1976 | Fukumaru | 260/566 R |
| 4,046,889 | 9/1977 | Ondetti et al. | 260/326.2 |
| 4,066,658 | 1/1978 | Felix | 260/326.2 |
| 4,116,962 | 9/1978 | Ondetti et al. | 260/455 R |

FOREIGN PATENT DOCUMENTS 8831 3/1980 European Pat. Off. ......... 260/326.4

OTHER PUBLICATIONS

R. Morrison et al., Org. Chem., 2nd edition (1967), p. 601.

*Primary Examiner*—Donald G. Daus
*Assistant Examiner*—M. C. Eakin

*Attorney, Agent, or Firm*—Stevens, Davis, Miller & Mosher

[57] ABSTRACT

This invention relates to a process for the optical resolution of DL-α-methyl-β-acylthiopropionic acids of the formula [I],

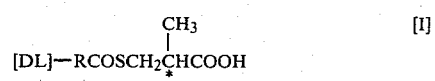

wherein R is a lower alkyl group having 1-4 carbon atoms, phenyl or substituted phenyl bearing methyl or chloro radical; a method for the racemization of an optically active α-methyl-β-acylthiopropionic acid of the formula [Ia],

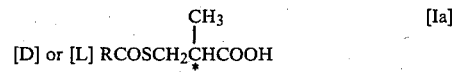

wherein R is as defined above; and a process for the synthesis of captopril of the formula [II],

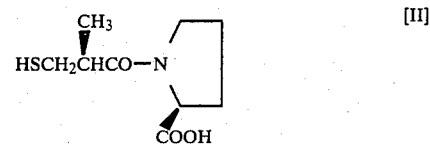

using the D-acid [Ia] as an intermediate.

The optically active α-methyl-β-acylthiopropionic acids are useful as intermediates for the production of medicines, for example, captopril or its congeners.

9 Claims, No Drawings

RESOLUTION OF MERCAPTOPROPIONIC ACIDS

The present invention relates to a process for the optical resolution of racemic carboxylic acids, the racemization of optically active carboxylic acids and the synthesis of an amide derivative.

More particularly, this invention relates to a process for the optical resolution of DL-α-methyl-β-acylthiopropionic acids of the formula [I],

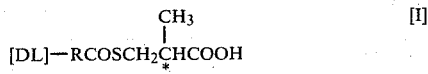

wherein R is a lower alkyl group having 1-4 carbon atoms, phenyl or substituted phenyl bearing methyl or chloro radical.

Further, this invention relates to a method for the racemization of an optically active α-methyl-β-acylthiopropionic acid of the formula [Ia],

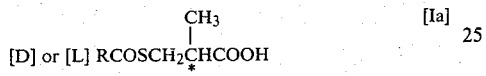

wherein R is as defined above.

The third aspect of this invention relates to a process for the synthesis of captopril of the formula [II],

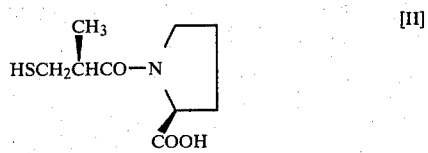

using the D-acid [Ia] as an intermediate.

The optically active α-methyl-β-acylthiopropionic acids resolved according to the process of the present invention are useful as intermediates for the production of medicines (e.g., captopril or its congeners).

Generally, the optical resolution of dl-carboxylic acids has been accomplished according to an ordinary fractional crystallization of diastereoisomeric salts consisting of optically active carboxylic acids and optically active amines such as quinidine, cinchonidine, brucine, ephedrine or α-methylbenzylamine.

In the case of DL-α-methyl-β-acylthiopropionic acids, however, it was difficult to carry out such optical resolutions by using these conventional resolution reagents. For example, solubility difference between a D-acid-ephedrine salt and L-acid-ephedrine salt was so light in various solvents that it was difficult to separate the diastereoisomeric salts from each other by fractional crystallization, and presevering fractional crystallization of the diastereosiomeric salts could separae the D-acid salt from the L-acid salt in only a low optical yield.

The present inventors further tried optical resolution of DL-α-methyl-β-acylthiopropionic acid by using optically active quinidine, α-methylbenzylamine and brucine. However, the fractional crystallization of the resulting diastereosiomers and the recovery of the said amines required complicated and troublesome treatment. Probably due to such difficulties, no reports concerning the synthesis or the property of the optically active acid [Ia] has been recorded in the literature before the present inventors achieved the present invention.

Under such circumstances as mentioned above, the present inventors have found, unexpectedly, that optically active amines of the formula [III],

wherein R₁ is methyl and R₂ is α-naphthyl or R₁ is

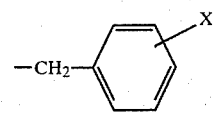

and R₂ is

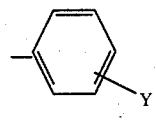

(wherein X and Y are each hydrogen, methyl or halogen) are very effective reagents for the optical resolution of DL-α-methyl-β-acylthiopropionic acids [I].

Thus the present invention provides a process for the optical resolution of DL-α-methyl-β-acylthiopropionic acid, which comprises contacting a DL-α-methyl-β-acylthiopropionic acid of the formula,

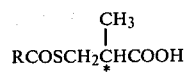

wherein R is a lower alkyl, phenyl or substituted phenyl bearing methyl or chloro radical, with an optically active amine of the formula,

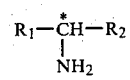

wherein R₁ is methyl and R₂ is α-naphthyl or R₁ is

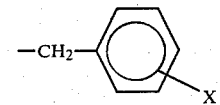

and R₂ is

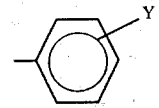

(wherein X and Y are each hydrogen, methyl or halogen) to form diastereoisomeric salts, subjecting the formed diastereoisomeric salts to the fractional crystallization in an organic solvent to separate the D-acid salt from the L-acid salt, and then contacting the individual diastereoisomeric salt with an acid to give D-α-methyl- β-acylthiopropionic acid and L-α-methyl-β-acylthiopropionic acid. Further the present invention provides a method for racemizing an optically active α-methyl-β-acylthiopropionic acid of the formula,

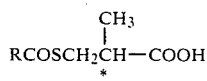

wherein R is a lower alkyl, phenyl or substituted phenyl bearing methyl or chloro radical, which comprises heating an optically active α-methyl-β-acylthiopropionic acid of the above mentioned formula in the presence of an effective amount of a salt of a carboxylic acid with an inorganic or organic base.

Still further, the present invention provides a process for producing captopril of the formula,

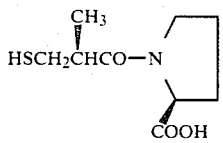

which comprises (A) contacting DL-α-methyl-β-acylthiopropionic acid of the formula,

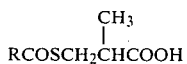

wherein R is lower alkyl, phenyl or substituted phenyl bearing methyl or chloro radical, with an optically active amine of the formula,

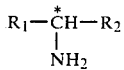

wherein $R_1$ is methyl and $R_2$ is α-naphthyl or $R_1$ is

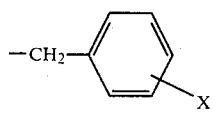

and $R_2$ is

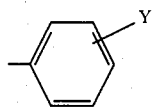

(wherein X and Y are each hydrogen, methyl or halogen) to form diastereoisomeric salts, subjecting the salts to fractional crystallization to separate the D-acid salt from the L-acid salt, and then contacting the thus obtained D-acid salt with an acid to give D-α-methyl-β-acylthiopropionic acid, (B) reacting the resulting D-α-methyl-β-acylthiopropionic acid with thionyl chloride to form its acid chloride, subjecting the resulting acid chloride to condensing reaction with L-proline in the presence of a base to give N-(D-α-methyl-β-acylthiopropionyl)-L-proline, and (C) deacylating the resulting N-(D-α-methyl-β-acylthiopropionyl)-L-proline with a base to give N-(D-α-methyl-β-thiopropionyl)-L-proline.

DL-acid [I] may be prepared by the procedures as described in U.S. Pat. No. 4,046,889.

Racemic amines of the optically active amines [III] are known by U.S. Pat. Nos. 3,954,870, 3,739,019 or by the copending U.S. patent application Ser. No. 65,429 now abandoned. Optically active amine [III] can be obtained by the procedures as described in copending U.S. patent application Ser. No. 90,479 which is a continuation-in-part application of U.S. patent application Ser. No. 65,429, now abandoned. For example, α-(o-, m- or p-chlorophenyl)-β-phenylethylamine can be optically resolved using L-(+)-tartaric acid to give optically active α-(o-, m- or p-chlorophenyl)-β-phenylethylamine.

The present invention may be carried out by the following procedures.

One mole of the DL-acid [I] and 0.5-1 mole, preferably 1 mole of the l-amine [III] are contacted in an inert reaction medium to form diastereoisomeric salts.

In the case of using less than 1 mole of the l-amine, an optically inactive amine or inorganic alkali may be used supplementarily.

The inert reaction medium used may be acetone, methylethylketone, methanol, ethanol, isopropanol or an aqueos mixture of them, or ethyl acetate, toluene, acetonitrile and their mixture.

The reaction may be carried out at a temperature ranging from −20° C. to the boiling point of the solvent used.

By the procedure described above, one of the diastereosiomeric salt (mostly the D-acid-l-amine salt) crystallizes from the reaction medium, and it can be separated by filtration. The relatively less soluble diastereoisomeric salt thus obtained may be further purified by recrystallization. On the other hand, the relatively more soluble diastereoisomeric salt can be isolated by the ordinary method, for example, by concentrating the filtrate and then collecting the residual crystals.

The separated D-acid salt and L-acid salt are individually contacted with an acid in a conventional manner to give the objective optically active D-acid and L-acid and to recover the l-amine.

The acid may be used in an amount of 1.5-3 moles for one mole of the salt and examples of the acid include hydrochloric acid or sulfuric acid.

Among the optically active amines [III], the optically active amines [IIIa] of the formula,

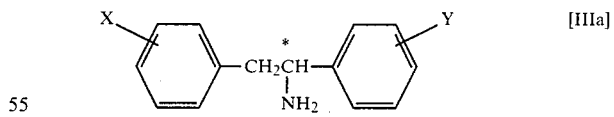

(wherein X and Y are as defined above) are preferable.

Examples of the optically active amine [III] are illustrated as follows:

β-(p-tolyl)-α-phenylethylamine
α,β-diphenylethylamine
β-(p-chlorophenyl)-α-phenylethylamine
α-(p-chlorophenyl)-β-phenylethylamine
1-(α-naphthyl)-ethylamine It has been known that optically active carboxylic acids, which possess an asymmetric carbon atom at α-position, are easily racemized on treatment with strong bases. However, the optically active acids [Ia] of this invention can not be racemized by the conventional procedures, because a decomposition reaction easily occurs owing to the unstable acylthio group involved in the acid [Ia].

The present inventors found a method for the racemization of the acid [Ia], which comprises heating the acid [Ia] in the presence of a salt of a carboxylic acid with an inorganic base or an organic base.

The salts of a carboxylic acid used in the present method are those of lower fatty acid (e.g., sodium acetate, potassium acetate, calcium acetate), or an aromatic acid (e.g., sodium benzoate). The salts of a carboxylic acid with an organic base may also be used for the present method. A tertiary amine such as 1,5-diazabicyclo[5,4,0]undec-5-ene(DBU) or triethylenediamine(-Dabco) is preferably used as the salt-forming organic base.

Salts of the acid [Ia] itself (e.g.,

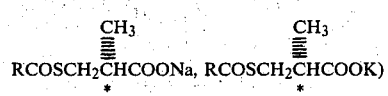

may also be used for the same purpose.

The amount of the salt or the organic base used is not limited, but preferably 0.05–1 equivalent may be used.

The reaction temperature may be 100°–200° C.

The solvent may be an inert solvent such as toluene or xylene.

The racemized acid [I] may be obtained from the reaction mixture by the conventional procedures (acidification with acid and extraction with toluene or ether).

The present inventors found that the D-acid [Ia] obtained above can be used as intermediates for captopril.

That is, captopril is now known to be useful as an antihypertensive agent, because it inhibits angiotensin converting enzyme and possesses remarkable antihypertensive activity. [Biochemistry, 16 5487 (1977)].

A typical synthesis method of the compound having the formula [II] is disclosed in Japanese Patent Kokai (Laid-Open) No. 52-116457 as follows.

An amidation reaction between DL-α-methyl-β-acylthiopropionic acid derivative and L-proline gives a mixture of two kinds of diastereoisomer having the formulas [II'] and [II''],

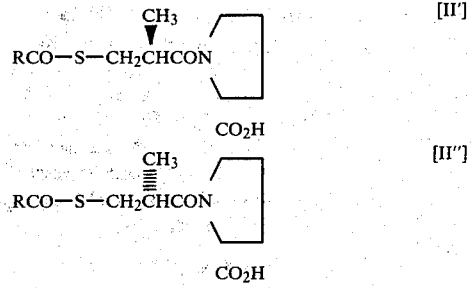

After isolating the D-type propionyl compound of the formula [II'], the acyl group represented by R—CO— is removed to obtain the objective compound [II].

It is considered that the above method has a drawback forming almost an equal amount of L-type propionyl compound of the formula [II''] as a by-product, and the expensiveness of the L-proline as a starting material amplifies such drawback. Under such circumstances, the present inventors have found the fact that the drawback forming the undesired diastereomer of the formula [II''] as a by-product can be avoided by employing a preliminarily resolved D-type compound of the formula [Ia] in place of the DL-α-methyl-β-acylthiopropionic acid of the formula [I].

That is, it has been confirmed that the product obtained from the D-type propionic acid derivative of the formula [Ia] as a starting material by converting to an acid chloride derivative and then condensing with L-proline by applying the most economical condensation process of the Schotten-Baumann type reaction, substantially gives only the objective compound of the formula [II'], and thus, the process of the present invention has been accomplished.

As the above result, it can be said that the process of the present invention for effectively obtaining the D-α-methyl-β-acylthiopropionic acid of the formula [Ia] provides an economically advantageous process for preparing N-(D-α-methyl-β-mercaptopropionyl)-L-proline (captopril) having the formula [II] which is a most useful antihypertensive agent.

According to the present invention, captopril can be obtained by the following procedures:

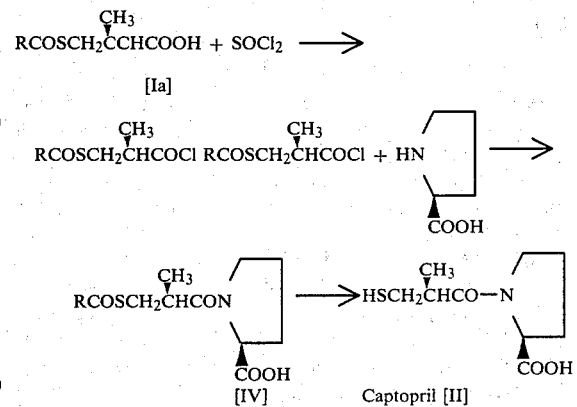

In carrying out the process of the present invention the acid halide of the D-acid [Ia] is condensed with L-proline in the presence of a base to give the compound of the formula [IV], which is then deacylated to give objective captopril [II].

The condensation reaction may be carried out under the ordinary Schotten-Baumann reaction condition.

The reaction may be carried out in the presence of a solvent such as water, methanol, ethanol, butanol, ether, tetrahydrofuran, acetone, methylethylketone, toluene or a mixture of them.

The base used may be a tertiary amine such as triethylamine or pyridine or alkali hydroxide such as sodium hydroxide or potassium hydroxide.

The reaction may be carried out at a temperature ranging from −10° to 30° C., preferably under ice cooling.

The objective [IV] is isolated by the conventional procedures.

The deacylation reaction of the compound [IV] is achieved under acidic condition or basic condition.

The acid used may be hydrochloric acid, sulfuric acid, phosphoric acid or p-toluenesulfonic acid.

The base used may be alkali or alkaline earth hydroxide or alkali carbonate. Ammonia may preferably be used.

The reaction solvent may be water, methanol, ethanol, butanol, acetone and methylethylketone etc.

Captopril may be isolated and purified by the conventional procedures.

The following examples illustrate details of this invention. However it should be understood that it is not intended to limit the present invention thereto.

EXAMPLE 1

Into a solution of DL-α-methyl-β-acetylthiopropionic acid (11.4 g) in acetonitrile (70 ml), was added 1-β-(p-tolyl)-α-phenylethylamine (14.5 g) at room temperature.

After stirring overnight, the precipitated D-α-methyl-β-acetylthiopropionic acid 1-β-(p-tolyl)-α-phenylethylamine salt [yield 15.6 g, mp. 113°–116° C., $[\alpha]_D^{20} - 73.6°$ (C=1.39, MeOH)] was obtained by filtration.

Recrystallization from methanol-isopropylether gave pure salt [yield 9.8 g, mp. 120°–121° C., $[\alpha]_D^{20} - 90.0°$ (C=1.2, MeOH)].

The salt (9.5 g) thus obtained was dissolved in 3% aqueous hydrochloric acid and extracted by diethylether to afford D-α-methyl-β-acetylthiopropionic acid as an oily substance, [3.6 g, $[\alpha]_D^{20} - 44.1°$ (C=2.4, CHCl$_3$)].

EXAMPLE 2

Into a solution of DL-α-methyl-β-acetylthiopropionic acid (16.2 g) in acetonitrile (120 ml), was added d-β-(p-tolyl)-α-phenylethylamine (19.7 g).

After stirring overnight, there precipitated the L-α-methyl-β-acetylthiopropionic acid.d-β-(p-tolyl)-α-phenylethylamine salt [20 g, mp. 117°–120° C., $[\alpha]_D^{20} + 75.3°$ (C=1.0, MeOH)].

The filtrate was condensed to dryness to afford D-rich-acid salt, which was dissolved in 3% aqueous hydrochloric acid and extracted with diethylether. The ether layer was condensed and a residual oily substance was dissolved in acetonitrile followed by adding 1-β-(p-tolyl)-α-phenylethylamine (9.8 g). After stirring overnight, the precipitated D-α-methyl-β-acetylthiopropionic acid.1-β-(p-tolyl)-α-phenylethylamine salt [7 g, mp. 118°–123° C., $[\alpha]_D^{20} - 90.8°$ (C=0.59, MeOH)] was obtained.

EXAMPLE 3

Into a solution of DL-α-methyl-β-acetylthiopropionic acid (3.41 g) in isopropyl alcohol (20 ml), was added a solution of pyridine (0.63 g) and 1-β-(p-tolyl)-α-phenylethylamine (2.48 g) in isopropylalcohol (10 ml). The precipitate was filtered to afford D-α-methyl-β-acetylthiopropionic acid.1-β-(p-tolyl)-α-phenylethylamine salt [3.05 g, mp. 111°–114.5° C. $[\alpha]_D^{20} - 78.8°$ (C=1.01, MeOH)].

EXAMPLE 4

Into a solution of DL-α-methyl-β-acetylthiopropionic acid (40.6 g) in water (250 ml) and acetone (220 ml), was added a solution of 1-β-(p-tolyl)-α-phenylethylamine (52.8 g) in acetone (30 ml) at room temperature followed by stirring for 3 hr.

The precipitate was filtered to afford D-α-methyl-β-acetylthiopropionic acid.1-β-(p-tolyl)-α-phenylethylamine salt [41.0 g, m.p. 118°–119° C., $[\alpha]D^{20} - 87.8°$ (C=1.0, MeOH)].

D-acid salt (1 g) thus obtained was decomposed with 3% hydrochloric acid and extracted with diethylether to afford D-α-methyl-β-acetylthiopropionic acid as an oily substance, [0.4 g, $[\alpha]_D^{20} - 38.6°$ (C=1.0, CHCl$_3$)].

EXAMPLE 5

Into a solution of DL-α-methyl-β-benzoylthiopropionic acid (2.24 g) in 95% methanol (10 g), was added a solution of 1-β-(p-tolyl)-α-phenylethylamine (2.12 g) in 95% methanol (10 g) at room temperature followed by stirring for 4 hr.

The precipitate was filtered to obtain D-α-methyl-β-benzoylthiopropionic acid 1-β-(p-tolyl)-β-phenylethylamine salt [2.39 g, mp. 153°–156° C., $[\beta]_D^{20} - 78.5°$ (C=1.0, MeOH)]. Recrystallization from 95% methanol gave the pure salt [1.65 g, m.p. 165°–166° C., $[\alpha]_D^{20} - 85.1°$ (C=1.0, MeOH)].

The salt (0.75 g) thus obtained was decomposed with 3% hydrochloric acid and extracted with diethylether to afford D-α-methyl-β-benzoylthiopropionic acid [0.35 g, mp. 69.5°–71° C., $[\alpha]_D^{20} - 62.1°$ (C=1.0, CHCl$_3$)].

EXAMPLE 6

Into a solution of DL-α-methyl-β-benzoylthiopropionic acid (18.0 g) in acetone (280 ml), was added a solution of d-β-(p-tolyl)-α-phenylethylamine (15.7 g) in acetone (50 ml) at room temperature followed by stirring for 4 hr. The precipitate was filtered to afford L-α-methyl-β-benzoylthiopropionic acid·d-α-(p-tolyl)-β-phenylethylamine salt [17.6 g, mp. 152°–154° C., $[\alpha]_D^{20} + 48.1$ (C=1.3, CHCl$_3$)]. The filtrate, which was obtained by filtration of the L-acid salt, was condensed under reduced pressure and the residue thus obtained was dissolved in toluene (60 ml) followed by standing overnight at room temperature. After stirring a further 2 hr under ice cooling, the precipitate was filtered to afford D-α-methyl-β-benzoylthiopropionic acid·d-β-(p-tolyl)-α-phenylethylamine salt [12.7 g, mp. 131°–132° C., $[\alpha]_D^{20} + 39.2°$ (C=1.3, MeOH)]. The D-acid salt (7.7 g) thus obtained was decomposed with 3% hydrochloric acid and extracted with toluene to afford D-α-methyl-β-benzoylthiopropionic acid [3.4 g, mp. 55°–59° C., $[\alpha]_D^{20} - 42.8°$ (C=1.2, CHCl$_3$)].

EXAMPLE 7

Into a solution of DL-α-methyl-β-benzoylthiopropionic acid (1.12 g) in toluene (25 ml), was added a solution of 1-β-(p-tolyl)-α-phenylethylamine (0.59 g) in toluene (25 ml). The precipitate was filtered to afford D-α-methyl-β-benzoylthiopropionic acid·1-β-(p-tolyl)-α-phenylethylamine salt [0.7 g, mp. 153.5°–156.5° C., $[\alpha]_D^{20} - 75.5°$ (C=1.00, MeOH)].

The D-acid salt thus obtained was decomposed with 3% aqueous hydrochloric acid and extracted with toluene to afford D-α-methyl-β-benzoylthiopropionic acid $[\alpha]_D^{20} - 32.4°$ (C=1.12, CHCl$_3$).

EXAMPLE 8

Into a solution of DL-α-methyl-β-acetylthiopropionic acid (0.49 g) in isopropyl alcohol (3 ml), was added a solution of 1-α,β-diphenylethylamine (0.59 g) in isopropylalcohol (3 ml). The precipitate was filtered to afford D-α-methyl-β-acetylthiopropionic acid·1-α,β-diphenylethylamine salt [0.31 g, mp. 101.5°–102.5° C. $[\alpha]_D^{20} - 76.2°$ (C=1.06, MeOH)].

The D-acid salt thus obtained was decomposed with 3% aqueous hydrochloric acid and extracted with diethylether to afford D-α-methyl-β-acetylthiopropionic acid as an oily substance $[\alpha]_D^{20} -30.5°$ (C=1.10, CHCl$_3$).

EXAMPLE 9

Into a solution of DL-α-methyl-β-benzoylthiopropionic acid (0.69 g) in toluene (15 ml), was added a solution of 1-α,β-diphenylethylamine (0.59 g) in toluene (15 ml). After cooling at 0° C., the precipitate was filtered to afford D-α-methyl-β-benzoylthiopropionic acid·1-α,β-diphenylethylamine salt [0.56 g, mp 130°–133° C., $[\alpha]_D^{20} -77.5°$ (C=0.98, MeOH)]. The D-acid salt thus obtained was decomposed with 3% hydrochloric acid and extracted with toluene to afford D-α-methyl-β-benzoylthiopropionic acid [mp. 54°–57° C., $[\alpha]_D^{20} -45.1°$ (C=0.95, CHCl$_3$)].

EXAMPLE 10

Into a solution of DL-α-methyl-β-(p-chlorobenzoyl)-thiopropionic acid (1.04 g) in ethanol (7 ml), was added a solution of 1-β-(p-tolyl)-α-phenylethylamine (0.85 g) in ethanol (3 ml). The precipitate was filtered to afford D-α-methyl-β-(p-chlorobenzoyl) thiopropionic acid·1-β-(p-tolyl)-β-phenylethylamine salt [1.41 g, mp. 154.5°–157.5° C., $[\alpha]_D^{20} -32.1°$ (C=1.02, DMF)]. Recrystallization from methanol gave the pure salt [1.1 g, mp. 166.5°–167.5° C., $[\alpha]_D^{20} -43.9°$ (C=1.0, DMF)].

The D-acid salt thus obtained was decomposed with 3% aqueous hydrochloric acid and extracted with toluene to afford D-α-methyl-β-(p-chlorobenzoyl) thiopropionic acid [mp. 79°–84° C., $[\alpha]_D^{20} -36.5°$ (C=1.01, CHCl$_3$)].

EXAMPLE 11

Into a solution of DL-α-methyl-β-(p-methylbenzoyl)-thiopropionic acid (0.95 g) in acetone (7 ml), was added a solution of 1-β-(p-tolyl)-α-phenylethylamine (0.85 g) in acetone (3 ml).

The precipitate was filtered to afford D-α-methyl-β-(p-methylbenzoyl)-thiopropionic acid·1-β-(p-tolyl)-α-phenylethylamine salt (0.95 g), [mp. 137°–142.5° C., $[\alpha]_D^{20} -39.7°$ (C=1.01, DMF)].

The D-acid salt was decomposed with 3% aqueous hydrochloric acid and extracted with toluene to afford D-α-methyl-β-(p-methylbenzoyl)-thiopropionic acid [mp. 71°–79° C., $[\alpha]_D^{20} -34.1°$ (C=0.98, CHCl$_3$)].

EXAMPLE 12

Into a solution of DL-α-methyl-β-acetylthio-propionic acid (0.17 g) in acetonitrile (2 ml), was added 1-β-(p-chlorophenyl)-α-phenylethylamine (0.21 g) at room temperature. The precipitate was filtered to afford D-α-methyl-β-acetylthiopropionic acid·1-β-(p-chlorophenyl)-α-phenylethylamine salt [0.21 g, mp. 90°–92° C., $[\alpha]_D^{20} -77°$ (C=0.5, MeOH)].

The D-acid salt thus obtained was decomposed and extracted with ether to afford D-α-methyl-acetylthiopropionic acid, $[\alpha]_D^{20} -2.5°$ (C=1.9, CHCl$_3$).

EXAMPLE 13

Into a solution of DL-α-methyl-β-benzoylthiopropionic acid (0.23 g) in ethanol (1.5 ml), was added 1-β-(p-chlorophenyl)-α-phenylethylamine (0.23 g) at room temperature. The precipitate was filtered to afford D-α-methyl-β-benzoylthiopropionic acid·1-β-(p-chlorophenyl)-α-phenylethylamine salt [0.26 g, mp. 143°–148° C., $[\alpha]_D^{20} -79.3°$ (C=0.8, MeOH)].

The D-acid salt thus obtained was treated with the similar procedures as described in example 10 to afford D-α-methyl-β-benzoylthiopropionic acid [mp. 52°–56° C., $[\alpha]_D^{20} -40.4°$ (C=1.3, CHCl$_3$)].

EXAMPLE 14

According to similar procedures as mentioned in Example 13 using acetone instead of ethanol, D-α-methyl-β-benzoylthiopropionic acid·1-β-(p-chlorophenyl)-α-phenylethylamine salt (mp. 143°–149° C.), and D-α-methyl-β-benzoylthiopropionic acid [mp. 54°–59° C., $[\alpha]_D^{20} -44.4°$ (C=1.2, CHCl$_3$)] were obtained.

EXAMPLE 15

Into a solution of DL-α-methyl-β-(p-chlorobenzoyl)-thiopropionic acid (0.26 g) in ethanol (2 ml), was added 1-β-(p-chlorophenyl)-β-phenylethylamine (0.23 g) at room temperature.

The precipitate was filtered to afford D-α-methyl-β-(p-chlorobenzoyl)-thiopropionic acid·1-β-(p-chlorophenyl)-α-phenylethylamine salt [0.32 g, mp. 140°–145° C., $[\alpha]_D^{20} -72.2°$ (C=1.7, MeOH)].

The D-acid salt thus obtained was decomposed with 3% aqueous hydrochloric acid and extracted with ethyl acetate to afford D-α-methyl-β-(p-chlorobenzoyl) thiopropionic acid (mp. 87°–89° C., $[\alpha]_D^{20} -22.6°$ (C=0.6, CHCl$_3$)].

EXAMPLE 16

Into a solution of DL-α-methyl-β-(p-methylbenzoyl)-thiopropionic acid (0.24 g) in acetone (2 ml), was added 1-β-(p-chlorphenyl)-α-phenylethylamine (0.23 g) at room temperature.

The precipitate was filtered to afford D-α-methyl-β-(p-methylbenzoyl)-thiopropionic acid·1-β-(p-chlorophenyl)-α-phenylethylamine salt [0.27 g, mp. 139°–148° C., $[\alpha]_D^{20} -78.0$ (C=1.1, MeOH)].

The D-acid salt thus obtained was decomposed with 3% aqueous hydrochloric acid and extracted with ethyl acetate to afford D-α-methyl-β-(p-methylbenzoyl)-thiopropionic acid [mp. 75°–78° C., $[\alpha]_D^{20} -57.7°$ (C=0.40, CHCl$_3$)].

EXAMPLE 17

Into a solution of DL-α-methyl-β-benzoylthiopropionic acid (1.12 g) in acetone (3 ml), was added a solution of 1-1-(α-naphthyl)-ethylamine (0.86 g) in acetone (2 ml).

The precipitate was filtered to afford D-α-methyl-β-benzoylthiopropionic acid·1-1-(α-naphthyl)-ethylamine salt [1.07 g, mp. 122°–127° C., $[\alpha]_D^{20} -19.7°$ (C=1.0, MeOH)].

The D-acid salt thus obtained was decomposed with 3% hydrochloric acid and extracted with toluene to afford, D-α-methyl-β-benzoylthiopropionic acid $[\alpha]_D^{20} -25.6°$ (C=0.99, CHCl$_3$).

EXAMPLE 18

According to similar procedures as mentioned in example 17, using isopropylalcohol instead of acetone, D-α-methyl-β-benzoylthiopropionic acid·1-1-(α-naphthyl)-ethylamine salt [1.2 g, mp. 121°–127° C., $[\alpha]_D^{20} -14.1°$ (C=1.00, MeOH)] and D-α-methyl-β-benzoylthiopropionic acid $[\alpha]_D^{20} -16.1°$ (C=0.95, CHCl$_3$) were obtained.

EXAMPLE 19

Into a solution of DL-α-methyl-β-benzoylthiopropionic acid (0.23 g) in acetone (2 ml), was added 1-α-(p- chlorophenyl)-β-phenylethylamine (0.23 g) at room temperature.

The precipitate was filtered to afford L-α-methyl-β-benzoylthiopropionic acid·1-α-(p-chlorophenyl)-β-phenylethylamine salt [0.20 g, mp. 136°–139° C., $[\alpha]_D^{20} - 86.1°$ (C=1.2, MeOH)].

The L-acid salt thus obtained was decomposed with 3% aqueous hydrochloric acid and extracted with diethylether to afford L-α-methyl-β-benzoylthiopropionic acid [mp. 52°–57° C., $[\alpha]_D^{20} + 42.1°$ (C=1.3, CHCl₃)].

EXAMPLE 20

A solution of L-α-methyl-β-benzoylthiopropionic acid [0.40 g, $[\alpha]_D^{20} + 55.9°$ (C=1, CHCl₃)] and DBU (55 mg) in xylene (3 ml) was refluxed for 1.5 hr.

After removing DBU with 3% hydrochloric acid, the racemic α-methyl-β-benzylthiopropionic acid $[\alpha]_D^{20} + 5.7°$ (C=1.6, CHCl₃) was obtained.

According to similar procedures as mentioned in Example 20, the following results were obtained.

| Optically active starting material | Base | Reaction condition | Optical rotation of Racemic product |
|---|---|---|---|
| L-α-methyl-β-benzoylthio-propionic acid $[\alpha]_D^{20} + 48.1°$ (C = 1, CHCl₃) | CH₃COONa | Xylene reflux 1.5 hr | $[\alpha]_D^{20} + 3.8°$ (C = 1.1, CHCl₃) |
| L-α-methyl-β-acetylthio-propionic acid $[\alpha]_D^{20} + 38.0°$ (C = 1.1, CHCl₃) | CH₃COONa | Xylene reflux 1.5 hr | $[\alpha]_D^{20} + 2.8°$ (C = 1.0, CHCl₃) |
| L-α-methyl-β-benzoylthio-propionic acid $[\alpha]_D^{20} + 48.1°$ (C = 1, CHCl₃) | DBU* | 140° 1.5 hr | $[\alpha]_D^{20} + 0.9°$ (C = 0.8, CHCl₃) |
| L-α-methyl-β-benzoylthio-propionic acid $[\alpha]_D^{20} + 48.1°$ (C = 1, CHCl₃) | K₂CO₃ | Xylene reflux 1.5 hr | $[\alpha]_D^{20} + 4.9°$ (C = 1.9, CHCl₃) |
| L-α-methyl-β-acetylthio-propionic acid $[\alpha]_D^{20} + 38.0°$ (C = 1.1, CHCl₃) | DBU | Xylene reflux 1.5 hr | $[\alpha]_D^{20} + 2.4°$ (C = 1.3, CHCl₃) |
| L-α-methyl-β-benzoylthio-propionic acid $[\alpha]_D^{20} + 43.5°$ (C = 1, CHCl₃) | NaH | Xylene reflux 1.5 hr | $[\alpha]_D^{20} + 2.4$ (C = 1.1, CHCl₃) |

*DBU; 1.5-diazabicyclo[5,4,0]undec-5-ene

EXAMPLE 21

Into D-α-methyl-β-acetylthiopropionic acid [3.2 g, $[\alpha]_D^{20} - 38.0°$ (C=1.0, CHCl₃)] obtained with the similar procedures as mentioned in Example 1, was added thionyl chloride (15 ml) under ice cooling followed by stirring overnight at room temperature.

After removing the excess thionyl chloride under reduced pressure, there was added benzene (4 ml) into the residue, and the product was evaporated to afford an objective acid chloride (3.5 g) as an oily substance.

Into a solution of L-proline (3.0 g) in aqueous sodium hydroxide [sodium hydroxide (0.95 g) in water (15 ml)], was added the acid chloride above obtained (3.5 g) in tetrahydrofuran (5 ml) under ice cooling during addition of 3N-sodium hydroxide to adjust the reaction mixture pH at 10–11.

After addition of the acid chloride, the reaction mixture was stirred for 3 hr at room temperature while adjusting the reaction mixture to pH 9–10 with 3N-sodium hydroxide.

The reaction mixture was washed with ether, adjusted to a pH of 2 with conc. hydrochloric acid and saturated with sodium chloride.

The objective substance was extracted with ethyl acetate.

Evaporation of the solvent gave N-(D-α-methyl-α-acetylthiopropionyl)-L-proline [4.76 g, mp. 74°–77° C., $[\alpha]_D^{20} - 121.3°$ (C=2.4, EtOH)].

According to similar procedures as mentioned above, the following compound was obtained.

N-(D-α-methyl-β-benzoylthiopropionyl)-L-proline as an oily substance $[\alpha]_D^{20} - 130°$ (C=1.1, EtOH).

EXAMPLE 22

N-(D-α-methyl-β-acetylthiopropionyl)-L-proline (3.2 g) was dissolved in 20% ammonia-methanol (35 ml) and stirred overnight at room temperature.

The reaction solution was evaporated under reduced pressure, to which was added 5% aqueous ammonia (15 ml), was washed with diethyl ether, acidified with potassium bisulfate and extracted with ethyl acetate to afford N-(D-α-methyl-β-mercaptopropionyl)-L-proline (2.5 g) as an oily substance.

According to similar procedures, N-(D-α-methyl)-β-mercaptopropionyl)-L-proline [mp. 77°–80° C., $[\alpha]_D^{20} - 130.6°$ (C=0.82, EtOH)] was obtained from N-(D-α-methyl-β-benzoylthiopropionyl)-L-proline.

What we claim is:

1. A process for the optical resolution of DL-α-methyl-β-acylthiopropionic acid, which comprises contacting a DL-α-methyl-β-acylthiopropionic acid of the formula,

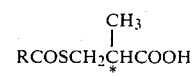

wherein R is a lower alkyl, phenyl or substituted phenyl bearing a methyl or chloro radical, with an optically active amine of the formula,

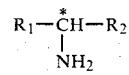

wherein R₁ is methyl and R₂ is α-naphthyl or R₁ is

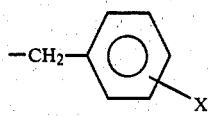

and R₂ is

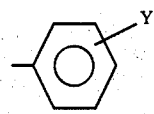

(wherein X and Y are each hydrogen, methyl or halogen) to form diastereoisomeric salts, subjecting the formed diastereoisomeric salts to fractional crystallization in an organic solvent to separate the D-acid salt from the L-acid salt, and then contacting the individual diastereoisomeric salts with acid to give D-α-methyl-β-acylthiopropionic acid and L-α-methyl-β-acylthiopropionic acid.

2. A process according to claim 1, wherein the DL-α-methyl-β-acylthiopropionic acid and the optionally active amine are used in equimolar amount.

3. A process according to claim 1, wherein the optically active amine is

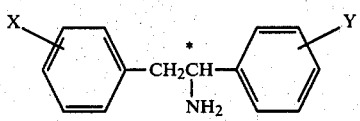

wherein X and Y are each hydrogen, methyl or halogen.

4. A process according to claim 1 or 3, wherein the optically active amine is
β-(p-tolyl)-α-phenylethylamine.

5. A process according to claim 1 or 3, wherein the optically active amine is
α,β-diphenylethylamine.

6. A process according to claim 1 or 3, wherein the optically active amine is
β-(p-chlorophenyl)-α-phenylethylamine.

7. A process according to claim 1 or 3, wherein the said optically active amine is
α-(p-chlorophenyl)-β-phenylethylamine.

8. A process according to claim 1, wherein the optically active amine is
1-(α-napthyl)-ethylamine.

9. A process for producing captopril of the formula,

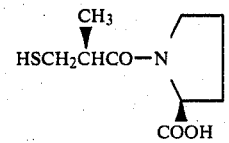

which comprises (A) contacting DL-α-methyl-β-acylthiopropionic acid of the formula,

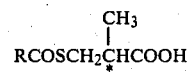

wherein R is lower alkyl, phenyl or substituted phenyl bearing methyl or chloro radical with an optically active amine of the formula,

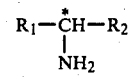

wherein R₁ is methyl and R₂ is α-naphthyl or R₁ is

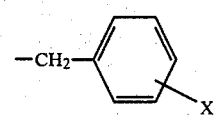

and R₂ is

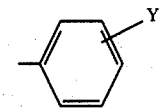

(wherein X and Y are each hydrogen, methyl or halogen) to form diastereoisomeric salts, subjecting the product to fractional crystallization to separate the D-acid salt from the L-acid salt, and then contacting the thus obtained D-acid salt with an acid to give D-α-methyl-β-acylthiopropionic acid, (B) reacting the resulting D-α-methyl-β-acylthiopropionic acid with thionyl chloride to form its acid chloride, subjecting the resulting acid chloride to condensing reaction with L-proline in the presence of a base to give N-(D-α-methyl-β-acylthiopropionyl)-L-proline, and (C) deacylating of the resulting N-(D-α-methyl-β-acylthiopropionyl)-L-proline with a base to give N-(D-α-methyl-β-thiopropionyl)-L-proline.

* * * * *